United States Patent [19]

Dahms

[11] 4,019,862
[45] Apr. 26, 1977

[54] CO₂ MEASUREMENT AND REAGENTS THEREFOR

[75] Inventor: Harald Dahms, Ossining, N.Y.

[73] Assignee: Corning Glass Works, Corning, N.Y.

[22] Filed: June 23, 1976

[21] Appl. No.: 698,868

[52] U.S. Cl. ............................ 23/230 B; 252/408
[51] Int. Cl.² ...................................... G01N 33/16
[58] Field of Search .................... 23/230 B, 253 R; 252/408

[56] References Cited

UNITED STATES PATENTS

| | | | |
|---|---|---|---|
| 3,556,950 | 1/1971 | Dahms | 23/230 B |
| 3,639,829 | 2/1972 | Harnoncourt | 23/230 B |
| 3,681,255 | 8/1972 | Wilfore | 252/408 |
| 3,874,850 | 4/1975 | Sorensen et al. | 23/230 B |
| 3,973,912 | 8/1976 | Trafton | 23/230 B |

*Primary Examiner*—R.E. Serwin

[57] ABSTRACT

Reagent compositions for use in $CO_2$ analysis which comprise certain acids and/or buffered acids together with selected additives. The acids and buffered acids have pH less than 4 and a vapor pressure not in excess of 10mm mercury. Examples of these acids include lactic acid, citric acid, phosphoric acid, sulfuric acid, perchloric acid, malic acid, malonic acid, oxalic acid, naphthalenesulfonic acid, picric acid, sulfamic acid, and nitric acid. The additives, which can be used separately or with one another, are ethers of fatty alcohols and polyoxyethylene (having the structure $R-O-(C_2H_4-O)_nH$), glycerin, polyvinyl alcohol, and pH sensitive indicator dyes, including methyl red, p-nitrophenol, neutral red, phenolphthalein, and o-cresolphthalein. An improved method for analysis of $CO_2$ in body fluids comprises the steps of adding these reagents to body fluid samples to release $CO_2$ therefrom into a gas space, displacing the released $CO_2$ to a detector, and measuring the amount of released $CO_2$ in the detector. Generally, acid reagents including at least one of the ethers of fatty alcohols and polyoxyethylene are preferable for releasing $CO_2$ from a body fluid sample.

35 Claims, No Drawings

$CO_2$ MEASUREMENT AND REAGENTS THEREFOR

BACKGROUND OF THE INVENTION

1. Field of the Invention

This invention relates to improved reagents for use in $CO_2$ analysis and to improved methods for determination of $CO_2$ in body fluids using these reagents.

2. Description of the Prior Art

The determination of blood gases is important for clinical analysis. In particular, the determination of carbon dioxide ($CO_2$) content is whole blood and blood serum are among the most frequently performed analyses in a clinical laboratory. Due to the great important of these analyses, a number of techniques have been developed and they are presently being used to determine $CO_2$ concentration.

A traditional technique used for the determination of $CO_2$ in blood is the method of D. D. Van Slyke, which was published in the Journal of Biological Chemistry, Volume 61, p. 523 (1924). In the basic Van Slyke method, blood serum and acid are mixed in a closed vessel and the carbon dioxide in the blood is extracted from the blood by application of a vacuum. The extracted carbon dioxide is then measured volumetrically or manometrically. When the vacuum is drawn, other blood gases are released from the serum in addition to the carbon dioxide. This requires that a base, such as sodium hydroxide, be added in order to separate the carbon dioxide from the other released gases. After this, the volumetric measurement is performed by known techniques.

In order to overcome some of the disadvantages attendant to the practice of the Van Slyke method, Applicant herein has filed a copending application Ser. No. 524,793 (filed Nov. 18, 1974) now U.S. Pat. No. 3,964,564, which allows very rapid determination of $CO_2$ content in body fluids. In that improved technique an equilibrated substantially stationary system is used to obtain very accurate results using only very small samples. That apparatus is automatically cleaned after each measurement and a blood gas measured by the detector has essentially the same composition as that originally established in the reactive vessel in which the body fluid is mixed with the $CO_2$ releasing reagent. Thus, that invention provides low cost, reliable measurement of $CO_2$ without the need for vacuums and measurements are made under stationary equilibrium conditions. Only small sample volumes are required, and very quick measurements are made.

In the method of aforementioned Ser. No. 524,793, a small amount of body fluid sample is combined with a small amount of reagent in a closed vessel to release $CO_2$ from the body fluid into the gas space of the vessel. Release of $CO_2$ into the gas space is at atmospheric pressure. After the gas space has been equilibrated with the released gas, a displacement liquid (such as the reagent) is introduced into the reaction vessel, thereby pushing the equilibrated gas into a detector connected to the gas space of the reaction vessel. After the displacement of some of the gas from the gas space into the detector, the detector measures the concentration of a sample of $CO_2$.

After the measurement is made, the mixture of sample and reagent in the closed vessel is drained from the vessel and excess flushing fluid (such as air) is passed through the detector and through the vessel in order to flush the apparatus prior to making another measurement.

Typically, the apparatus used to provide the improved method of $CO_2$ analysis described in Ser. No. 524,793 (U.S. Pat. No. 3,964,864) comprises a reaction vessel which can be closed after the sample and reagent are introduced, a reagent means for putting reagent into the reaction vessel, a displacement means for adding fluid to the reagent vessel to push the released gas to a detector, and a flushing means for cleansing the system after each measurement. Typically, mechanical means such as a rotary slide valve is used to connect these various functional units into the system at the proper time.

The most frequently used acid for the release of $CO_2$ from blood serum is lactic acid, in various concentrations such as 0.1M, 1.0M, or higher concentrations. Lactic acid such as this is used in particular as one of the preferred reagents in the apparatus of Ser. No. 524,793, now U.S. Pat. No. 3,964,864. Also, that application broadly suggests the use of detergents in the lactic acid.

For the best operation of apparatus for detection of $CO_2$, it has been discovered that the reagent must meet several requirements other than the basic requirement of releasing $CO_2$ from blood and blood serum. These other requirements are necessary for providing very high accuracy, precision, and speed for $CO_2$ determinations in a practical system. Thus, experimentation has led to the use of the compositions described herein for release of $CO_2$ from body fluids.

The requirements for preferred reagent compositions, which must be met in a practical system, include the following:

1. The $CO_2$ should be released from the body fluid in a minimum of time so that fast analysis can be made.

2. The reagent should release $CO_2$ from aqueous standard solutions (such as carbonate or bicarbonate solutions used for calibration) as fast as the reagent releases $CO_2$ from blood serum. Thus, when ordinary lactic acid reagent is used, lower readings of $CO_2$ will be obtained for aqueous solutions than for blood serum. In order to compensate for this, mixing times for aqueous solutions have to be longer in order to have complete release of the $CO_2$ therein.

3. After the analysis is complete, the apparatus has to be drained of the body fluid, such as blood serum. The use of plain lactic acid reagent over many analyses often results in the accumulation of remains from the blood serum so that clogging of the lines eventually will occur. Therefore, an improved reagent is needed to promote complete drainage in the testing apparatus.

4. Mechanical components are used in the apparatus to perform $CO_2$ analysis. These mechanical components are exposed to mechanical wear and tear which has to be minimized for long apparatus lifetime. For instance, slide valves often contain two flat plastic plates which rub on each other if there is no lubricant or gasket. In order to extend the life of the apparatus, the reagent should have lubricating properties.

5. The reagent solution should be chemically stable for long periods of time, preferably for many months.

6. A reagent solution should have a low solubility for $CO_2$ in order to have large output signal and accurate results.

7. It is also desirable that the reagent be such that it will provide an indication of whether or not the $CO_2$ measurement apparatus is performing properly. For example, the release of $CO_2$ from standards and from serum requires that a certain minimum amount of acid reagent be present. If smaller amounts are present due to a malfunction of the apparatus, the results will be incorrect (i.e., too low). Thus, in the practice of the present invention, indicator dyes which are pH sensitive are used to provide an indication of a malfunctioning apparatus. For example, sodium carbonate standard solutions have a pH of about 11. When an excess of acid is added, the pH drops to about 3 or 4. A malfunction of the apparatus which adds only insufficient amounts of acid may leave the pH at 10 or 11. Thus, the indicator would provide a color indication that such malfunction was present.

The preceding seven requirements were obtained as a result of extensive experimentation to determine how to maximize operation of $CO_2$ detectors whose operation is based on the Van Slyke technique. During this experimentation, many acids and additives were utilized. Some of these additives are more well known detergents, and each was tested with respect to the seven listed requirements. It was found that, while some of these modified reagents were satisfactory with respect to some of the requirements, only a limited class of acid reagents was suitable with respect to all of the requirements. This suitable class of reagents was not apparent from the use of surfactants, such as cleansers and detergents, in combination with and acid such as lactic acid. For example, many well known surfactants were combined with lactic acid and the resulting reagents tested, but these resulting reagents were found to be poor with respect to many of the performance standards. Thus, reagents comprising lactic acid and surfactants having the tradenames TWEEN-20, TWEEN-40, TWEEN-60, and TWEEN-80, available from J. T. Baker Chemical Company, Phillipsburg, New Jersey, have been found to yield poor results in this technique for $CO_2$ measurement. Other surfactants which have not performed well for this specific purpose include surfactants having the tradenames Span-20, Span-40, Span-60, Span-65, Span-80, and Span-85, available from City Chemical Corp., New York, N.Y. Esters of various materials have been also utilized with rather poor results. Consequently, considerable experimentation was required to discover suitable reagents for use in releasing $CO_2$ from bodyfluids, such as blood serum.

Accordingly, it is a primary object of the present invention to provide improved reagents for release of $CO_2$ from body fluids.

It is another object of the present invention to provide improved reagents for releasing $CO_2$ from body fluids, which reagents will release the $CO_2$ quickly and will act as lubricants in the apparatus used for $CO_2$ detection.

It is still another object of the present invention to provide improved reagents for release of $CO_2$ from body fluids, where the reagents will release $CO_2$ from aqueous standard solutions used for calibration as quickly as they will release $CO_2$ from samples of body fluids.

It is a further object of the present invention to provide reagents for release of $CO_2$ from body fluids, using reagents which enhance drainage in the apparatus used to detect $CO_2$.

It is a still further object of the present invention to provide improved reagents for releasing $CO_2$ from body fluids, where the reagents have lubricating properties.

It is another object of the present invention to provide an improved method for detecting $CO_2$ in body fluids, using improved reagents.

It is another object of the present invention to provide reagents for release of $CO_2$ from body fluids, which reagents provide an indication of apparatus malfuncton in the apparatus used for such analysis.

It is a further object of this invention to provide improved reagents for release of $CO_2$ from body fluids, where the reagents have a low solubility for $CO_2$.

BRIEF SUMMARY OF THE INVENTION

Reagents are described which provide improved release of $CO_2$ from body fluids such as whole blood, blood serum, plasma, etc. These reagent compositions are used for $CO_2$ analysis and comprise certain acids and buffered acids together with selected additives. The acids and buffered acids have pH less than 4 and a vapor pressure not in excess of 10mm mercury. Examples of these acids include lactic acid, citric acid, phosphoric acid, sulfuric acid, perchloric acid, malic acid, malonic acid, oxalic acid, napthanlenesulfonic acid, picric acid, sulfamic acid, and nitric acid. The additives, which can be used separately or with one another, are ethers of fatty alcohols and plyoxyethylene (having the structure $R-O-(C_2H_4-O)_nH$), glycerin, polyvinylalcohol, and pH sensitive indicator dyes, including methyl red, p-nitrophenol, neutral red, phenolphthalein, and o-cresolphthalein. An improved method for analysis of $CO_2$ in body fluids comprises the steps of adding these reagents to body fluid samples to release $CO_2$ therefrom into a gas space, displacing the released $CO_2$ to a detector, and measuring the amount of released $CO_2$ in the detector. Generally, acid reagents including at least one of the ethers of fatty alcohols and polyoxyethylene are preferable for releasing $CO_2$ from a body fluid sample. Also, lactic acid is the preferred acid for releasing $CO_2$.

Other suitable reagents are those comprising the aforementioned acids or buffered acids, the aforementioned ethers of fatty alcohols and polyoxyethylene, and suitable pH sensitive dyes, such as methyl red, p-nitrophenol, neutral red, phenolphthalein, and o-cresolphthalein. These are dye indicators which change color in the pH range between 11 and 3.

Other suitable reagents are those which comprise the aforementioned acids and buffered acids and the aforementioned dyes singly or in combination, without the ethers of fatty alcohols and polyoxyethylene, or glycerin or polyvinyl alcohol.

In the practice of this invention, an improved method for releasing $CO_2$ from body fluids comprises the steps of adding one of the aforementioned reagents to a sample of body fluid to release $CO_2$ therefrom into a gas space, displacing said released $CO_2$ to a detector, and measuring a sample (usually stationary) of said $CO_2$ in said detector. A suitable but not limiting apparatus for the performance of this method is that shown in aforementioned Ser. No. 524,793. (U.S. Pat. No. 3,964,864).

The acids and buffered acids herein must have this low pH (less than 4) in order that $CO_2$ be released efficiently and rapidly from the sample being tested. These acids and buffered acids must have a vapor pressure not in excess of 10mm mercury in order to prevent vapors from the acid being released into the gas space along with $CO_2$. If acid vapors were released, they would be transported to the detector along with the $CO_2$, and would interfere with the $CO_2$ measurement.

In general, the ether additives are used at a concentration of greater than 1 gram per liter and less than 80 grams per liter. Glycerin is used in a concentration of more than 0.5 grams per liter and less than 40 grams per liter. Polyvinyl alcohol is used in concentrations of more than 2 grams per liter and less than 180 grams per liter.

These and other objects, features and advantages will be more apparent from the following more particular description of the preferred embodiments.

DETAILED DESCRIPTION OF THE PREFERRED EMBODIMENTS

This invention uses novel reagents to more quickly release $CO_2$ from body fluids. In addition, the reagents offer many advantages over existing reagents and are particularly suitable for use in apparatus where mechanical parts are subject to wear and tear during the analysis. Thus, the invention involves reacting a small amount of these reagents with a sample of body fluid, such as blood serum, in order to release $CO_2$. In the apparatus of Ser. No. 524,973, now U.S. Pat. No. 3,964,864, the $CO_2$ is released into a gas space at atmospheric pressure. The next step of the invention is to transfer the released $CO_2$ to a detector where a measurement is made of the amount of $CO_2$ released. In the preferred method, a displacing fluid is added to the reaction chamber to force the released $CO_2$ to the detector. Again, in the preferred method, the detector (such as thermal conductivity detector) measures a substantially stationary sample of the released $CO_2$. This result can be displayed or stored in medical records. After the measurement has been made, the apparatus is subjected to a flushing step in which the detector, connecting lines, and reaction vessel are drained and purged of any remaining gas samples or body fluid samples. A reverse flush using a large volume of air at atmospheric pressure is satisfactory.

In the practice of this invention, it is important that the $CO_2$ be released from the body fluid sample rapidly and completely in order to have fast, accurate results. It is also necessary that the release of $CO_2$ from the body fluid sample be the same as that from samples used for calibrating the $CO_2$ detection instrument. Further, after analysis the apparatus has to be drained of blood serum. The use of plain lactic acid often results in the accumulation of remains from blood serum which causes clogging in the apparatus. The reagent should be one that will promote proper draining and cleansing of the apparaus, while having a low solubility for $CO_2$.

In the typical measurement apparatus, mechanical components are subject to wear and generally used reagents do not have lubricating qualities for reduction of this wear. Additionally, it is difficult to be able to modify the reagents and still have them be chemically stable over long periods of time. The reagents found for use in accordance with this invention meet these requirements and are distinguished from common reagents in use.

Accordingly, the present invention reagents comprise certain acids and buffered acids of a particular class of acids together with certain additives which may be used singly or in combination with one another. These acids have a pH less than 4 and a vapor pressure not in excess of 10mm mercury. This limited class of acids include lactic acid, citric acid, phosphoric acid, sulfuric acid, perchloric acid, malic acid, malonic acid, oxalic acid, picric acid, naphthalenesulfonic acid, sulfamic acid, and nitric acid. The additives are the following: (1) ethers of fatty alcohols and polyoxyethylene given by the structure $R—O—(C_2H_4—O)_nH$, (2) glycerin, (3) polyvinyl alcohol, and (4) pH sensitive dyes such as methyl red, p-nitrophenol, neutral red, phenolphthalein, and o-cresolphthalein. Lactic acid is the preferred acid, and the best reagents include at least one ether of a fatty alcohol and ployoxyethylene. Representative reagents which perfrom well in $CO_2$ analysis will be given below.

A number of members of this class have been successfully tested with respect to all prerequisites of a successful reagent. Ethers which have been successfully tested include the following:

|  |  | Common Name |
|---|---|---|
| R-Lauryl | n = 23 | Polyoxyethylene (23) laurylether |
| R-Cetyl | n = 20 | Polyoxyethylene (20) cetylether |
| R-Oleyl | n = 10 | Polyoxyethylene (10) oleylether |
| R-Oleyl | n = 20 | Polyoxyethylene (20) oleylether |

Representative compositions comprising lactic acid and these ethers are the following:

| 1) | Lactic acid, | 2 moles/liter plus | 0.5 weight % | | Polyoxyethylene (20) cetylether |
| --- | --- | --- | --- | --- | --- |
| 2) | " | 2 moles/liter/plus | 5 | " | Polyoxyethylene (20) cetylether |
| 3) | " | 0.1 moles/liter plus | 0.5 | " | Polyoxyethylene (23) laurylether |
| 4) | " | 2.0 moles/liter plus | 5.0 | " | Polyoxyethylene (23) laurylether |
| 5) | " | 2.0 moles/liter plus | 0.5 | " | Polyoxyethylene (10) oleylether |
| 6) | " | 2.0 moles/liter plus | 5.0 | " | Polyoxyethylene (10) oleylether |
| 7) | " | 2.0 moles/liter plus | 5.0 | " | Polyoxyethylene (20) oleylether |
| 8) | " | 2.0 moles/liter plus | 0.5 | " | Polyoxyethylene (20) oleylether |

In general, the strength of the lactic acid can be between 0.2 moles/liter and 3.5 moles/liter while the weight percentage of the ether which is added can be between 1 gram/liter and 90 grams/liter. Preferably, the ether concentration is greater than 1 gram/liter and less than 80 grams/liter. Further, other additives can be used together with these ethers for other purposes.

When glycerin is used as an additive, it is present in a concentration of more than 0.5 gram per liter and less than 40 grams per liter. Polyvinyl alcohol is used in concentrations of more than 2 grams per liter and less than 180 grams per liter.

Another constituent which can be present in the reagents mentioned above or can be present along with the acid is an indicator dye of the type which is pH sensitive, usually between pH 3 and pH 11. These dyes are used in the apparatus to determine when insufficient amounts of acid are present and are, for example, methyl red, p-nitrophenol, neutral red, phenolphthalein, and o-cresolphthalein. These are well known, commercially available dyes. They are added to the acid in amounts typically less than 0.1 grams/liter. If used in the acid reagent together with the acid and the aforementioned ethers, the amounts of such indicator dyes are the following: methyl red 2mg/l, p-nitrophenol 10mg/l, neutral red 1mg/l, phenolphthalein 5mg/l, o-cresolphthalein 4mg/l.

Certain indicator dyes can also be used in the reagents described above, or separately with plain acid or buffered acid. These indicators tell whether or not the $CO_2$ measuring apparatus is performing properly and also provide other benefits.

For the release of $CO_2$ from standards and from body fluids, a certain amount of acid is necessary. If smaller amounts of acid are present due to any type of malfunction of the apparatus, the results will be incorrect since insufficient amounts of $CO_2$ will be released. This is especially apparent when standard solutions are used since they are often basic. In order to properly calibrate the measuring apparatus, an excess of acid must be added to drop the pH to about 3 or 4. Thus, if the indicator dye is one which changes color at about this low pH, and indication will be provided that a sufficient amount of acid is present for $CO_2$ release. On the other hand, if the indicator is not present and the pH does not lower sufficiently, it will not be possible to tell that the apparatus is operating incorrectly. This means that a number of samples might be tested inaccurately before it is realized that improper readings are resulting.

To alleviate this problem, the reagents described herein include pH sensitive indicator dyes. These have been mentioned previously and are typically those which change their color in the pH range between 11 and 3. The examples stated previously were methyl red, p-nitrophenol, neutral red, phenolphthalein, and o-cresolphthalein. These indicators are present in the reagent in an amount sufficient to provide visual indication of color change when the pH of the reagent changes. Typical amounts of these indicators used in the reagent have already been mentioned.

In addition to the sample reagent compositions given above, the following reagents have been successfully tested with respect to all of the requirements which a reagent must satisfy.

1. A reagent comprising lactic acid, 1% by weight glycerin, and 4% by weight polyoxyethylene (23) laurylether. This has been found to be slightly superior to the same solution without the glycerin.

2. A reagent comprising 2M lactic acid and 3% by weight glycerin. This was superior to a reagent containing only 2M lactic acid.

3. A reagent containing 2M lactic acid, 0.8% by weight polyvinylalcohol, and 4% by weight polyoxyethylene (23) laurylether. This reagent was superior to a reagent solution containing only 2M lactic acid and 4% by weight of this ether.

4. A reagent solution containing 2M lactic acid and 0.8% by weight polyvinyl alcohol. This solution was superior to a plain solution of 2M lactic acid.

5. A reagent solution containing 1 mole of sulfuric acid per liter (equal to 98 grams of sulfuric acid per liter) and 50 grams of polyoxyethylene (23) laurylether. Neither the concentration of the acid nor that of the additive was critical. The acid concentration was raised to 1.6 moles per liter and lowered to 0.5 moles per liter, without adversely affecting the test results. Likewise, the concentration of the additive was raised to 80 grams and lowered to 10 grams, without adversely affecting the test results.

6. When phosphoric acid was used instead of sulfuric acid, at a concentration of 1 mole per liter, good test results were also obtained.

7. In the reagent solution of example 5 above, the ether additive was replaced by 50 grams per liter of polyoxyethylene (20) cetylether. Similar good test results were obtained.

8. In the practice of the present invention, a suitable acid reagent is one comprising lactic acid, nitric acid, and polyvinyl alcohol. As an example, a reagent solution containing 0.1M nitric acid, 2M lactic acid, and polyvinyl alcohol in the concentration between 2 and 180 grams per liter mentioned previously.

TEST PROCEDURES

The various reagents described here and considerable numbers of other reagents were used in the apparatus of Ser. No. 524,793 (U.S. Pat. No. 3,964,864) in order to test these reagents with respect to the criteria mentioned previously. In some cases, pure lactic acid solutions were used. Aqueous sodium carbonate standard solutions and blood serum of known $CO_2$ content were tested using different reagents. The carbon dioxide analyzer was run for ten seconds, using pure lactic acid and several other reagents, including those described herein. The read-out on the apparatus was noted as a measure of the fraction of $CO_2$ released in this short time.

The results of these tests showed that the reagents using ethers of fatty alcohols and polyoxyethylene performed considerably between than other reagents, for both the aqueous standard solutions and for the blood serum. In fact, the improved reagents of the present disclosure released almost twice as much carbon dioxide from the aqueous standard and from the serum solutions in this time period. Additionally, the reagents of this invention provided read-outs from the aqueous standard and from the blood serum samples which were approximately the same. In contrast with this, prior art reagents and reagents using such chemicals as Span and Tween did not perform as well in this test and the difference between the readings for the aqueous standard solutions and the blood serum solutions was more pronounced.

The testing showed that the reagents comprising lactic acid and the ethers of polyoxyethylene with various fatty alcohols were most effective in accelerating the $CO_2$ release and for providing read-outs from the standard solutions and from the blood serum samples that were approximately the same.

In order to check the promotion of drainage of blood serum from the apparatus after analysis, twenty blood serum samples were analyzed and the reaction chamber was then inspected for remains which had not been drained. The same reagents were used as were used in the test to establish the effectiveness of release of $CO_2$. These reagents included lactic acid at a concentration of 2 moles/l with additives at a 5% concentration of sorbitan monosterate, polyoxyethylene (23) laurylether and polyoxyethylene (10) oleylether.

Again, the reagents described in this application were effective in preventing protein build-up in the test apparatus, while the reagent with sorbitan monosterate was not.

In order to determine the effect of the reagents on wear and tear of mechanical parts in the apparatus, the apparatus was run continuously for twenty four hours with each reagent solution. Thus, a total of about 1800 analyses were performed. The slide valve mechanism, which was the mechanical part subject to most wear in the test apparatus, was then disassembled and inspected for wear. Since the slide valve initially had a mirror finish, any disappearance of that mirror finish in operation provided an indication of wear.

The results of this wear test showed that the reagents of the present invention were most effective in all aspects of wear reduction. This reagent class included lactic acid and ethers of fatty alcohols and polyoxyethylene. These are equally effective over a wide range of lactic acid concentrations. Also, the concentration of the ether additives is not critical. Both 0.5 and 5% concentrations are equally effective.

In addition to these factors, the subject reagents provide low solubility for $CO_2$, and chemical stability for long periods of time, where such periods are measured in months. In contrast with this, lactic acid reagents including sorbitan monolaurate, or sorbitan monopalmitate, or sorbitan monostearate, or sorbitan stearate, sorbitan monooleate, and sorbitan triolate (known as Span compounds) were not suitable.

Thus, although detergents and surfactants have been used with acid reagents previously, the particular requirements stated herein for successful reagents did not allow ready application of these surfactants and detergents with lactic acid reagent and other acids used to release $CO_2$ from body fluid samples. In accordance with Applicant's extensive experimentation, only the reagents described herein perform successfully with respect to all of the required criteria. These more successful reagents included those comprising certain acids and selected additives as described herein. Also, the dyes specified herein can be used individually with these acids to provide reagents having beneficial effects beyond that which would be thought to happen when a color indicator was used.

Thus, improved reagents for $CO_2$ analysis have been described and an improved method for $CO_2$ detection using these reagents is provided. These reagents can be used in different types of apparatus for the detection of $CO_2$ and will provide results heretofore unknown when conventional reagents have been used.

What is claimed is:

1. An acid reagent for use in clinical analysis comprising an acid having a pH less than 4 and a vapor pressure not in excess of 10 mm mercury and an ether of fatty alcohol and polyoxyethylene having the structure $R-O-(C_2H_4-O)_nH$.

2. The reagent of claim 1, where said acid is selected from the class consisting of lactic acid, citric acid, sulfuric acid, phosphoric acid, perchloric acid, malic acid, malonic acid, naphthalenesulfonic acid, oxalic acid, picric acid, sulfamic acid, and nitric acid.

3. The reagent of claim 1, where said acid is a buffered acid.

4. The reagent of claim 1, further including glycerin.

5. The reagent of claim 1, further including polyvinyl alcohol.

6. The reagent of claim 1, where said ethers are present in a concentration greater than 1 gram per liter and less than 80 grams per liter.

7. The reagent of claim 1, further including an indicator dye being pH sensitive in the range $3 \leq pH \leq 11$.

8. The reagent of claim 7, where said dyes are selected from the class comprising methyl red, p-nitrophenol, neutral red, phenolphthalein, and o-cresolphthalein.

9. A method for analyzing $CO_2$ in body fluids comprising the steps of
adding an acid reagent to a sample of said body fluid to release $CO_2$ therefrom into a gas space, said reagent being comprised of an acid having a pH less than 4 and a vapor pressure not in excess of 10mm mercury together with an ether of a fatty alcohol and polyoxyethylene having the structure $R-O-(C_2H_4-O)_nH$, and
displacing said released $CO_2$ to a detector where a sample of said $CO_2$ is measured.

10. An acid reagent for use in releasing species from body fluids comprising an acid selected from the class consisting essentially of lactic acid, phosphoric acid, sulfuric acid, perchloric acid, citric acid, malic acid, malonic acid, naphthalenesulfonic acid, oxalic acid, picric acid, sulfamic acid, and nitric acid, and an ether of fatty alcohols and polyoxyethylene, said ether having the structure $R-O-(C_2H_4-O)_nH$.

11. The reagent of claim 10 where said ether is present in a concentration greater than 1 gram per liter and less than 80 grams per liter.

12. The reagent of claim 10, further including glycerin.

13. The reagent of claim 10, further including polyvinyl alcohol.

14. The reagent of claim 10, further including a pH sensitive dye.

15. The reagent of claim 14, where said dye is selected from the class consisting essentially of methyl red, p-nitrophenol, neutral red, phenolphthalein, and o-cresolphthalein.

16. The reagent of claim 10, where said acid is buffered.

17. A method for analyzing $CO_2$ in a sample of body fluid, comprising the steps of:
adding an acid reagent to a sample of body fluid to release $CO_2$ therefrom into a gas space, said reagent comprising an acid selected from the class consisting essentially of lactic acid, phosphoric acid, sulfuric acid, perchloric acid, citric acid, malic acid, malonic acid, naphthalenesulfonic acid, oxalic acid, picric acid, sulfamic acid, and nitric acid, and an ether of fatty alcohol and polyoxyethylene, said ether having the structure $R-O-(C_2H_4-O)_nH$,
displacing said released $CO_2$ to a detector, and measuring a sample of said released $CO_2$.

18. An acid reagent used to analyze constituents in body fluids, said reagent including an acid having pH less than 4 and a vapor pressure not in excess of 10mm mercury together with a pH sensitive dye which is sensitive to pH in the range of pH 3 to about pH 11.

19. The reagent of claim 18, where said dye is selected from the class consisting essentially of methyl red, p-nitrophenol, neutral red, phenolphthalein, and o-cresolphthalein.

20. The reagent of claim 19, where said dye is present in an amount less than 0.1 grams per liter.

21. A method for analyzing $CO_2$ in a sample of body fluid comprising the steps of:
combining an acid reagent with said body fluid sample to release $CO_2$ into a gas space, said reagent comprising an acid having pH less than 4 and a vapor pressure not in excess of 10mm mercury plus a pH sensitive dye which is sensitive to pH in the range of about pH 3 to about pH 11.
displacing said released $CO_2$ to a detector, and measuring said released $CO_2$ with said detector.

22. An acid reagent for use in releasing species from body fluids comprising lactic acid together with an ether of fatty alcohol and polyoxyethylene, said ether having the structure $R-O-(C_2H_4-O)_nH$.

23. The reagent of claim 22, where said ether is present in a concentration greater than 1 gram per liter and less than 80 grams per liter.

24. The reagent of claim 22, further including a pH sensitive dye.

25. The reagent of claim 22, further including glycerin.

26. The reagent of claim 22, further including polyvinylalcohol.

27. The reagent of claim 22, where said lactic acid is buffered.

28. The reagent of claim 22, where said ethers are selected from the class consisting essentially of R-Lauryl, R-Cetyl, R-Oleyl ($n=10$), R-Oleyl ($n=20$).

29. A method for analyzing $CO_2$ in a sample of body fluid comprising the steps of:
 combining an acid reagent and said body fluid sample to release $CO_2$ into a gas space, said reagent comprising lactic acid together with an ether of fatty alcohol and polyoxyethylene having the structure $R-O-(C_2H_4-O)_nH$,
 displacing said released $CO_2$ to a detector and,
 detecting the amount of said released $CO_2$.

30. An acid reagent for use in releasing species from body fluids, comprising lactic acid and glycerin in a concentration greater than 0.5 grams per liter and less than 40 grams per liter.

31. An acid reagent for use in releasing species from body fluid samples, comprising lactic acid together with polyvinyl alcohol.

32. A method for analyzing $CO_2$ in a body fluid sample, comprising the steps of:
 combining an acid reagent and said body fluid sample to release $CO_2$ therefrom, said reagent comprising lactic acid and glycerin, and
 measuring said released $CO_2$ in a detector.

33. A method for analyzing $CO_2$ in body fluid samples, comprising the steps of:
 combining an acid reagent and said body fluid sample to release $CO_2$ therefrom, said reagent being comprised of lactic acid together with polyvinyl alcohol,
 displacing said released $CO_2$, and measuring said released $CO_2$ with a detector.

34. An acid reagent for use in releasing species from body fluids comprising lactic acid, nitric acid, and polyvinyl alcohol in a concentration between 2 and 180 grams per liter.

35. An acid reagent for use in releasing species from body fluids comprising nitric acid and polyvinyl alcohol in a concentration between 2 and 180 grams per liter.

* * * * *

UNITED STATES PATENT AND TRADEMARK OFFICE
CERTIFICATE OF CORRECTION

PATENT NO. : 4,019,862
DATED : April 26, 1977
INVENTOR(S) : Harald Dahms

It is certified that error appears in the above-identified patent and that said Letters Patent are hereby corrected as shown below:

Column 1, line 14, "important" should be -- importance --.

Column 1, line 37, "3,964,564" should be -- 3,964,864 --.

Column 2, line 64, "signal" should be -- signals --.

Column 3, line 28, "and" second occurrence, should be -- an --.

Column 3, line 47, "bodyfluids" should be -- body fluids --.

Column 5, line 62, delete "invention".

Column 7, line 16, "and" should be -- an --.

Column 8, line 26, "between" should be -- better --.

Signed and Sealed this ninth Day of August 1977

[SEAL]

Attest:

RUTH C. MASON
Attesting Officer

C. MARSHALL DANN
Commissioner of Patents and Trademarks